(12) United States Patent
Kim

(10) Patent No.: US 11,087,871 B2
(45) Date of Patent: Aug. 10, 2021

(54) METHOD FOR PREDICTING ANATOMICAL LANDMARKS AND DEVICE FOR PREDICTING ANATOMICAL LANDMARKS USING THE SAME

(71) Applicant: Ye Hyun Kim, Busan (KR)

(72) Inventor: Ye Hyun Kim, Busan (KR)

(73) Assignee: Ye Hyun Kim, Busan (KR)

( * ) Notice: Subject to any disclaimer, the term of this patent is extended or adjusted under 35 U.S.C. 154(b) by 175 days.

(21) Appl. No.: 16/505,518

(22) Filed: Jul. 8, 2019

(65) Prior Publication Data
US 2020/0035351 A1    Jan. 30, 2020

(30) Foreign Application Priority Data

Jul. 27, 2018 (KR) ......................... 10-2018-0088078

(51) Int. Cl.
| | | |
|---|---|---|
| *G16H 30/40* | (2018.01) | |
| *G16H 50/20* | (2018.01) | |
| *A61C 7/00* | (2006.01) | |
| *G06N 20/10* | (2019.01) | |
| *A61B 6/14* | (2006.01) | |
| *A61B 6/00* | (2006.01) | |
| *G06K 9/00* | (2006.01) | |
| *A61C 19/04* | (2006.01) | |

(52) U.S. Cl.
CPC .............. *G16H 30/40* (2018.01); *A61B 6/14* (2013.01); *A61B 6/5217* (2013.01); *A61C 7/002* (2013.01); *A61C 19/04* (2013.01); *G06K 9/00234* (2013.01); *G06N 20/10* (2019.01); *G16H 50/20* (2018.01)

(58) Field of Classification Search
None
See application file for complete search history.

(56) References Cited

U.S. PATENT DOCUMENTS

| | | | |
|---|---|---|---|
| 2004/0242987 A1* | 12/2004 | Liew ....................... | A61B 6/583 600/407 |
| 2011/0245951 A1* | 10/2011 | Gantes ............... | G05B 19/4099 700/98 |
| 2016/0001092 A1* | 1/2016 | Solehmainen ......... | A61N 2/006 600/9 |
| 2016/0328643 A1* | 11/2016 | Liu ......................... | G06N 3/084 |
| 2017/0007209 A1* | 1/2017 | Yoo ........................ | A61B 8/488 |
| 2018/0184989 A1* | 7/2018 | Inglese ................ | A61B 6/5217 |
| 2018/0228450 A1* | 8/2018 | Vega ....................... | A61B 6/032 |
| 2018/0253837 A1* | 9/2018 | Ghesu .................... | G06T 7/0012 |
| 2018/0333063 A1* | 11/2018 | Muchhala ........... | G01R 33/0354 |
| 2019/0328489 A1* | 10/2019 | Capron-Richard .......................... G06T 7/0012 | |
| 2020/0163589 A1* | 5/2020 | Takagi ................. | A61B 5/4519 |

* cited by examiner

*Primary Examiner* — Santiago Garcia
(74) *Attorney, Agent, or Firm* — Weaver Austin Villeneuve & Sampson LLP

(57) ABSTRACT

The present disclosure provides a method of predicting anatomical landmarks which includes: receiving a medical lateral head image of a subject; predicting landmarks in the medical lateral head image using a landmark prediction model configured to predict anatomical landmarks in the medical lateral head image; and providing an image with the landmark marked, and a device using the method.

13 Claims, 11 Drawing Sheets

| NUMBER | MEASUREMENT POINT | NUMBER | MEASUREMENT POINT | NUMBER | MEASUREMENT POINT |
|---|---|---|---|---|---|
| 1 | A point | 26 | Nasal bridge | 51 | Upper molar distal point |
| 2 | Anterior nasal spine | 27 | Orbitale | 52 | Upper molar mesial point |
| 3 | Antegonial notch | 28 | PM point | 53 | Upper embrasure |
| 4 | Articulare | 29 | Posterior nasal spine | 54 | Upper lip |
| 5 | B point | 30 | Porion | 55 | Mandibular outline 1 |
| 6 | Basion | 31 | Pogonion | 56 | Mandibular outline 2 |
| 7 | Cervical point | 32 | Pronasale | 57 | Mandibular outline 3 |
| 8 | Condylion | 33 | Pterygoid point | 58 | Mandibular outline 4 |
| 9 | Columella | 34 | R1 point | 59 | Mandibular outline 5 |
| 10 | Corpus Left | 35 | R3 point | 60 | Mandibular outline 6 |
| 11 | Dorsum of Nose | 36 | Ramus down | 61 | Maxilla outline 1 |
| 12 | Glabella | 37 | Sella | 62 | Maxilla outline 2 |
| 13 | Gnathion | 38 | Supradentale | 63 | Maxilla outline 3 |
| 14 | Gonion | 39 | Soft tissue A point | 64 | Maxilla outline 4 |
| 15 | Infradentale | 40 | Soft tissue B point | 65 | Maxilla outline 5 |
| 16 | Lower incisor crown tip | 41 | Soft tissue Gnathion | 66 | Maxilla outline 6 |
| 17 | Lower incisor root tip | 42 | Soft tissue Menton | 67 | Maxilla outline 7 |
| 18 | Lower molar distal point | 43 | Soft tissue Nasion | 68 | Maxilla outline 8 |
| 19 | Lower molar mesial point | 44 | Soft tissue Pogonion | 69 | Maxilla outline 9 |
| 20 | Labrale inferius | 45 | Stomion inferius | 70 | Maxilla outline 10 |
| 21 | Labrale superius | 46 | Stomion superius | 71 | Maxilla outline 11 |
| 22 | Lower embrasure | 47 | Submandibular point | 72 | Symphysis outline 1 |
| 23 | Lower lip | 48 | Subnasale | 73 | Symphysis outline 2 |
| 24 | Menton | 49 | Upper incisor crown tip | 74 | Symphysis outline 3 |
| 25 | Nasion | 50 | Upper incisor root tip | 75 | Symphysis outline 4 |

FIG. 4A

METHOD FOR PREDICTING ANATOMICAL LANDMARKS AND DEVICE FOR PREDICTING ANATOMICAL LANDMARKS USING THE SAME

CROSS-REFERENCE TO RELATED APPLICATIONS

This application claims the priority of Korean Patent Application No 10-2018-0088078 filed on Jul. 27, 2018, in the Korean Intellectual Property Office, the disclosure of which is incorporated herein by reference.

BACKGROUND

Field

The present disclosure relates to a method of predicting anatomical landmarks and a device for predicting anatomical landmarks using the same and, more particularly, a method of predicting anatomical landmarks, the method configured to predict anatomical measurement points that are used for orthodontic analysis, and a device using the method.

Description of the Related Art

In general, a malocclusion is referred to a state of a set of teeth being irregular and upper and lower teeth abnormally meeting. Such malocclusion may cause not only functional problems such as problems with mastication and pronunciation or aesthetic problems with the face, but also problems with health such as a carious tooth and a gum disease.

Orthodontic treatment can be performed as a method of changing malocclusion into occlusion.

Orthodontic analysis that is performed on a subject in the step of planning such as measuring the size of the maxillofacial frame, measuring the growth direction of the maxillofacial frame, and measuring the degree of protrusion of sets of teeth can be in close connection with the prognosis of the orthodontic treatment. In particular, it can be very important to find anatomical landmarks anatomically predetermined for measurement in terms of accurate planning of orthodontic treatment. To this end, medical personnel have had visually found anatomical landmarks on a medical lateral head image obtained from subjects and performed the pre-orthodontic treatment analysis described above. However, this method can be accompanied by a problem of deterioration in accuracy when devising a treatment plan because the positions of anatomical landmarks can be different, depending on the proficiency of medical personnel.

As accuracy in devising of a treatment plan before orthodontic treatment is increasingly required to improve the quality of medical services, it has been continuously required to develop a method of accurately detecting anatomical landmarks.

The description provided above as a related art of the present disclosure is to help understanding the background of the present disclosure. The description should not be construed as admitting that the description exists as the prior art.

SUMMARY

Meanwhile, in order to solve the problems described above, orthodontic analysis programs configured to programmatically perform pre-orthodontic treatment analysis have emerged. However, these orthodontic analysis programs can be troublesome for medical personnels because it is required to input all anatomical landmarks one by one. Further, according to the prior art, since medical personnel still have to find anatomical landmarks in person on the basis of a medical lateral head image, the accuracy in analysis may depend on the proficiency of medical personnel.

The inventor(s) of the present disclosure could recognize that it is possible to use a prediction model learned to predict landmarks for orthodontics on the basis of data of medical lateral head images as a method of solving the problems with the existing orthodontic analysis programs and increasing accuracy in pre-orthodontic treatment analysis.

As a result, the inventor(s) of the present disclosure has developed a new orthodontic analysis program that can provide information for orthodontic analysis by predicting the positions of anatomical landmarks for orthodontics in a medical lateral head image of a subject using a prediction model.

In more detail, the inventor(s) of the present disclosure addressed that the accuracy of prediction can increase when using two prediction models learned to predict a lateral facial region in a medical lateral head image and predict anatomical landmarks for measurement in the predicted lateral facial region.

As a result, it was possible to develop an orthodontic analysis system using a prediction model configured to predict a lateral facial region in a medical lateral head image and a prediction model configured to predict anatomical landmarks in the predicted lateral facial region.

Accordingly, an object of the present disclosure is to provide a method of predicting anatomical landmarks, the method being configured to predict landmarks in a medical image using a landmark prediction model configured to predict anatomical landmarks for measurement on the basis of a received medical lateral head image and to provide a prediction result.

Another object of the present disclosure is to provide a method of predicting anatomical landmarks, the method being configured to predict coordinates of a lateral facial region, using a lateral facial region prediction model configured to predict the lateral facial region in a medical lateral head image, and to predict landmarks in the lateral facial region using a landmark prediction model.

Another object of the present disclosure is to provide a method of predicting anatomical landmarks, the method being configured to measure at least one selected from the size of a maxillofacial frame, the growth direction of the maxillofacial frame, and the degree of protrusion of sets of teeth of a subject on the basis of predicted landmarks.

Another object of the present disclosure is to provide a device for predicting anatomical landmarks, the device including a receiver configured to receive a medical lateral head image of a subject and a processor operably connected with the receiver and configured to use various prediction models.

The objects of the present disclosure are not limited to the objects described above and other objects will be clearly understood by those skilled in the art from the following description.

In order to achieve the objects described above, a method of predicting anatomical landmarks according to an embodiment of the present disclosure is provided. The method includes: receiving a medical lateral head image of a subject; predicting landmarks in the medical lateral head image using a landmark prediction model configured to predict anatomical landmarks in the medical lateral head image; and providing an image with the predicted landmark marked.

According to an aspect of the present disclosure, the method of the present disclosure may further include predicting coordinates of a lateral facial region in the medical lateral head image using a lateral facial region prediction model configured to predict a lateral facial region in the medical lateral head image before predicting the landmarks. Further, predicting the landmarks may further include predicting landmarks in the lateral facial region using the landmark prediction model.

According to another aspect of the present disclosure, predicting the landmarks may include: predicting x-axial and y-axial coordinates of the landmarks in the lateral facial region, on the basis of the medical lateral head image and the coordinates of the predicted lateral facial region, using the landmark prediction model; and creating an xml, json, or csv file including the predicted landmarks and the x-axial and y-axial coordinates. Further, the providing of an image with the predicted landmark marked further includes providing an image with positions of the landmarks marked in the medical lateral head image on the basis of the medical lateral head image and the xml, json, or csv file.

According to another aspect of the present disclosure, the landmark prediction model can be a model learned to predict the landmarks in the medical lateral head image on the basis of a gradient boosting algorithm, and the lateral facial region prediction model can be a model learned to predict the lateral facial region in the medical lateral head image on the basis of a support vector machine algorithm (SVM).

According to another aspect of the present disclosure, the lateral facial region prediction model can be a model learned through receiving a medical lateral head image for learning with coordinates of a lateral facial region determined in advance, and predicting the lateral facial region in the medical lateral head image for learning on the basis of the coordinates of the lateral facial region and a pattern of the medical lateral head image for learning.

According to another aspect of the present disclosure, the medical lateral head image for learning can be an image obtained through HOG (Histogram of Oriented Gradient)-converting a sample medical lateral head image of a sample subject, and marking a lateral facial region in the HOG-converted sample medical lateral head image on the basis of the coordinates of the lateral facial region in the sample medical lateral head image and a path of the sample medical lateral head image.

According to another aspect of the present disclosure, the method of the present disclosure may further include measuring at least one selected from the size of the maxillofacial frame, the growth direction of the maxillofacial frame, and the degree of protrusion of sets of teeth of the subject on the basis of the predicted landmarks.

According to another aspect of the present disclosure, the method may further include converting the medical lateral head image into a monochrome image; and vectorizing the monochrome image when the received medical lateral head image is an RGB color image.

According to another aspect of the present disclosure, the vectorizing of the monochrome image may include: calculating brightness difference values between any pixel selected from a plurality of pixels of the monochrome image and a plurality of pixels adjacent to the predetermined pixel; and vectorizing the monochrome image toward a pixel having a largest brightness difference value from the predetermined pixel of the plurality of adjacent pixels.

According to another aspect of the present disclosure, the landmark can be at least one selected from the group consisting of an A-point, a B-point, an ANS (Anterior nasal spine), an AN (Antegonial notch), an articulare, a basion, a C (Cervical point), a condylion, a columella, a CL (Corpus Left), a dorsum of nose, a glabella, a gnathion, a gonion, an infradentale, an LICT (Lower incisor crown tip), an LIRT (Lower incisor root tip), an LMDP (Lower molar distal point), an LMMP (Lower molar mesial point), an Li (Labrale inferius), an Ls (Labrale superius), an LE (Lower embrasure), a lower lip, a menton, a nasion, a nasal bridge, an orbitale, a PM point, a PNS (Posterior nasal spine), a porion, a pogonion, a Pn (Pronasale), a Pt (Pterygoid point), an R1 point, an R3 point, an RD (Ramus down), a sella, an Sd (Supradentale), a soft tissue A point, a soft tissue B point, a Gn' (Soft tissue Gnathion), an Me' (Soft tissue Menton), an N' (Soft tissue Nasion), a Pg' (Soft tissue Pogonion), an Stmi (Stomion inferius), an Stms (Stomion superius), an SM point (Submandibular point), an Sn (Subnasale), a UICT (Upper incisor crown tip), a UIRT (Upper incisor root tip), a UMDP (Upper molar distal point), a UMMP (Upper molar mesial point), a UE (Upper embrasure), an upper lip, a mandibular outline 1, a mandibular outline 2, a mandibular outline 3, a mandibular outline 4, a mandibular outline 5, a mandibular outline 6, a maxilla outline 1, a maxilla outline 2, a maxilla outline 3, a maxilla outline 4, a maxilla outline 5, a maxilla outline 6, a maxilla outline 7, a maxilla outline 8, a maxilla outline 9, a maxilla outline 10, a maxilla outline 11, a symphysis outline 1, a symphysis outline 2, a symphysis outline 3, and a symphysis outline 4 that are determined in advance as lateral cephalometric landmarks for orthodontics.

According to another aspect of the present disclosure, the landmark prediction model can be a model learned by: receiving a medical lateral head image for learning with coordinates of a plurality of landmarks predetermined in advance for a lateral facial region; and predicting coordinates of the plurality of landmarks in the medical lateral head image for learning on the basis of a shape formed by the coordinates of a plurality of landmarks in the medical lateral head image for learning.

In order to achieve the objects described above, a device for predicting anatomical landmarks according to an embodiment of the present disclosure is provided. The device includes: a receiver configured to receive a medical lateral head image of a subject; and a processor operably connected to the receiver. The processor is configured to predict landmarks in the medical lateral head image busing a landmark prediction model configured to predict landmarks in the medical lateral head image.

According to an aspect of the present disclosure, the process can be further configured to predict coordinates of a lateral facial region in the medical lateral head image using a lateral facial region prediction model configured to predict a lateral facial region in the medical lateral head image, and to predict the landmarks in the lateral facial region using the landmark prediction model.

According to an aspect of the present disclosure, the process can be further configured to: predict x-axial and y-axial coordinates of the landmarks in the lateral facial region, on the basis of the medical lateral head image and the coordinates of the predicted lateral facial region, using the landmark prediction model; create a xml, json, or csv file including the predicted landmarks and the x-axial and y-axial coordinates; and provide an image with positions of the landmarks marked in the medical lateral head image on the basis of the medical lateral head image and the xml, json, or csv file.

According to an aspect of the present disclosure, the device for predicting of the present disclosure may further include a measurer configured to measure at least one selected from the size of the maxillofacial frame, the growth direction of the maxillofacial frame, and the degree of protrusion of sets of teeth of the subject on the basis of the predicted landmarks.

According to an aspect of the present disclosure, the device for predicting may further include a data preprocessor configured to convert the medical lateral head image into a monochrome image and vectorize the monochrome image when the received medical lateral head image is an RGB color image.

According to an aspect of the present disclosure, the data preprocessor can be configured to calculate brightness difference values between any pixel selected from a plurality of pixels of the monochrome image and a plurality of pixels adjacent to the predetermined pixel, and vectorize the monochrome image toward a pixel having a largest brightness difference value from the predetermined pixel of the plurality of adjacent pixels.

The present disclosure has an effect that can provide information for orthodontic analysis of a subject by providing a method of predicting anatomical landmarks using a lateral facial region prediction model configured to predict a lateral facial region in a medical lateral head image and a landmark prediction model configured to predict anatomical landmarks in the lateral facial region, and a device using the method.

In more detail, according to the present disclosure, it can be possible to devise an accurate treatment plan for the subject before orthodontics by predicting and providing anatomical landmarks that are measurement points for orthodontic analysis. Accordingly, the present disclosure can contribute to providing an accurate and effective orthodontic method suitable for each subject.

For example, as anatomical landmarks are provided, medical personnel can more accurately and easily measure the size of a maxillofacial frame, measure the growth direction of the maxillofacial frame, and analyze the degree of protrusion of sets of teeth.

Further, the present disclosure has an effect that can predict and provide measurement positions of anatomical landmarks in a received medical lateral head image with high accuracy regardless of the proficiency of medical personnel.

The present disclosure has an effect that can provide prediction information with high accuracy by processing and using a medical lateral head image for learning to learn a prediction model so that a lateral facial region is more accurately predicted in a medical lateral head image.

The effects of the present disclosure are not limited to those described above and more various effects are included in the specification.

BRIEF DESCRIPTION OF THE DRAWINGS

The above and other aspects, features and other advantages of the present disclosure will be more clearly understood from the following detailed description taken in conjunction with the accompanying drawings, in which:

FIGS. 4A to 4D show a procedure of creating medical lateral head image data for learning a landmark prediction model, the data being used in the method of predicting anatomical landmarks according to an embodiment of the present disclosure and the device for predicting anatomical landmarks using the method.

DETAILED DESCRIPTION OF THE EMBODIMENT

Figure 1A:
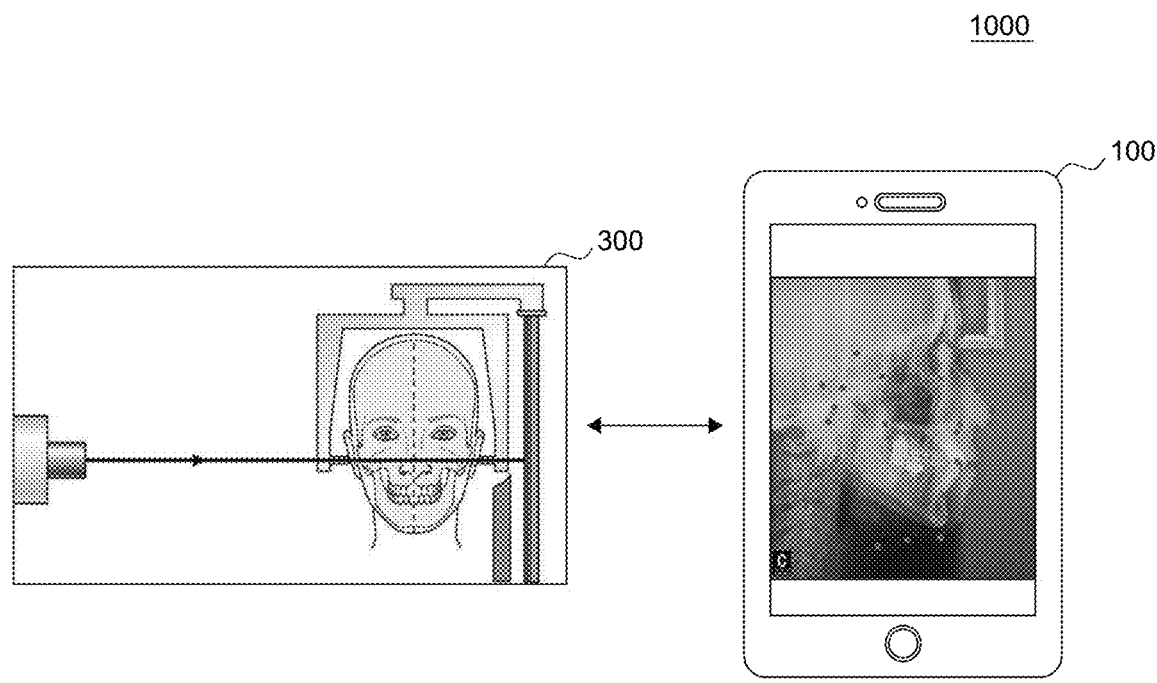
FIG. 1A shows an orthodontic analysis system using a device for predicting anatomical landmarks according to an embodiment of the present disclosure.

The advantages of the present disclosure and methods of achieving them will be clear by referring to the exemplary embodiments that will be described hereafter in detail with reference to the accompanying drawings. However, the present disclosure is not limited to the exemplary embodiments described hereafter and will be implemented in various ways, and the exemplary embodiments are provided to complete the description of the present disclosure and let those skilled in the art completely know the scope of the present disclosure and the present disclosure is defined by claims.

The shapes, sizes, ratios, angles, and numbers of articles disclosed in the drawings to describe embodiments of the present disclosure are only examples and the present disclosure is not limited to those shown in the drawings. Further, in the description of the present disclosure, detailed descriptions of well-known technologies will be omitted so as not to obscure the description of the present disclosure with unnecessary detail. When terms 'include', 'have', and 'composed of' are used herein, other components can be added unless 'only~' is used. When a component is expressed by singular, it includes plural unless specifically stated otherwise.

In analysis of a component, it is construed as including an error range even if it is not specifically described.

The features of embodiments of the present disclosure may be partially or entirely combined or mixed, may be technically integrated and driven in various ways to enable those skilled in the art to sufficiently understand them, and may be implemented independently from each other or in association with each other.

Terms to be used herein are defined hereafter to make the specification clear.

A term "medical lateral head image" that is used herein may mean all images including a lateral profile of a subject received from a medical image diagnosis apparatus. Preferably, the medical lateral head image disclosed herein can be a lateral cephalometric radiograph, but is not limited thereto. The medical lateral head image can be a 2-D image, a 3-D image, a cut of still image, or a moving image composed of a plurality of cuts. For example, when the medical lateral head image is a moving image composed of a plurality of cuts or frames, landmarks may be predicted for each of a plurality of medical lateral head images in accordance with a method of predicting anatomical landmarks according to an embodiment of the present disclosure. As a result, the present disclosure may provide real-time predicted information by performing prediction of anatomical landmarks simultaneously with reception of a medical lateral head image from an image diagnosis apparatus.

Meanwhile, the term "anatomical landmark" that is used herein may mean a landmark anatomically determined in advance as a measurement point for orthodontics. The anatomical landmark may be a lateral cephalometric landmark, but is not limited thereto.

Meanwhile, it can be very important to find anatomical landmarks when devising an accurate treatment plan for orthodontic treatment. A problem of deterioration in accuracy when devising a treatment plan may occur because the positions of anatomical landmarks to be determined can be different, depending on the proficiency of medical personnel.

In order to solve this problem, a prediction model learned to predict anatomical landmarks in a medical lateral head image can be used.

The term "landmark prediction model" that is used herein can be a model configured to predict the positions of landmarks for measurement in a medical lateral head image. For example, the landmark prediction model can be a model learned to predict landmarks in a received medical lateral head image on the basis of a gradient boosting algorithm. In more detail, the landmark prediction model can be a model learned by a step of predicting the coordinates of a plurality of landmarks in a medical lateral head image for learning on the basis of the shape formed by the coordinates of the plurality of landmarks in the medical lateral head image for learning.

The landmark can be at least one selected from the group consisting of an A-point, a B-point, an ANS (Anterior nasal spine), an AN (Antegonial notch), an articulare, a basion, a C (Cervical point), a condylion, a columella, a CL (Corpus Left), a dorsum of nose, a glabella, a gnathion, a gonion, an infradentale, an LICT (Lower incisor crown tip), an LIRT (Lower incisor root tip), an LMDP (Lower molar distal point), an LMMP (Lower molar mesial point), an Li (Labrale inferius), an Ls (Labrale superius), an LE (Lower embrasure), a lower lip, a menton, a nasion, a nasal bridge, an orbitale, a PM point, a PNS (Posterior nasal spine), a porion, a pogonion, a Pn (Pronasale), a Pt (Pterygoid point), an R1 point, an R3 point, an RD (Ramus down), a sella, an Sd (Supradentale), a soft tissue A point, a soft tissue B point, a Gn' (Soft tissue Gnathion), an Me' (Soft tissue Menton), an N' (Soft tissue Nasion), a Pg' (Soft tissue Pogonion), an Stmi (Stomion inferius), an Stms (Stomion superius), an SM point (Submandibular point), an Sn (Subnasale), a UICT (Upper incisor crown tip), a UIRT (Upper incisor root tip), a UMDP (Upper molar distal point), a UMMP (Upper molar mesial point), a UE (Upper embrasure), an upper lip, a mandibular outline 1, a mandibular outline 2, a mandibular outline 3, a mandibular outline 4, a mandibular outline 5, a mandibular outline 6, a maxilla outline 1, a maxilla outline 2, a maxilla outline 3, a maxilla outline 4, a maxilla outline 5, a maxilla outline 6, a maxilla outline 7, a maxilla outline 8, a maxilla outline 9, a maxilla outline 10, a maxilla outline 11, a symphysis outline 1, a symphysis outline 2, a symphysis outline 3, and a symphysis outline 4 that are determined in advance as lateral cephalometric landmarks for orthodontics, but is not limited thereto.

Meanwhile, the landmark prediction model can be a model learned to predict positions of landmarks on the basis of a medical image cropped to include only a lateral facial region that is the target of measurement in a medical lateral head image. For example, the landmark prediction model can be a model learned to predict x-axial and y-axial coordinates of landmarks in the lateral facial region on the basis of a medical lateral head image and the coordinates of a lateral facial region. By this learning method, the landmark prediction model can predict landmarks with higher accuracy than when it is configured to predict landmarks in the entire medical lateral head image.

The term "lateral facial region prediction model" that is used herein may be a model configured to predict a lateral facial region including the lateral facial part that is the target region to be measured for orthodontics in a medical lateral head image. For example, the lateral facial region prediction model can be a model learned to predict the lateral facial region in the medical lateral head image on the basis of a support vector machine algorithm. In more detail, the lateral facial region prediction model can be a model learned to receive a medical lateral head image with predetermined coordinates of a lateral facial region, and predict the lateral facial region in the medical lateral head image for learning on the basis of the coordinates of the lateral facial region and a pattern of the medical lateral head image for learning.

The "lateral facial region" may have pixel values and texture that are different from other regions, for example, a background region. Accordingly, the lateral facial region prediction model may predict a lateral facial region on the basis of pixel values or texture.

Meanwhile, the medical lateral head image can be an image acquired using a step of HOG (Histogram of Oriented Gradient)-converting a sample medical lateral head image of a sample subject and marking a lateral facial region in the HOG-converted sample medical lateral head image on the basis of the coordinates of the lateral facial region in the sample medical lateral head image and the path of the sample medical lateral head image. However, the medical lateral head image for learning is not limited thereto.

The prediction models that are used in various embodiments of the present disclosure, as described above, can be used independently or in a combination in prediction of anatomical landmarks.

Hereinafter, an orthodontic analysis system using a device for predicting anatomical landmarks according to an embodiment of the present disclosure and a device for predicting anatomical landmarks are described with reference to FIGS. 1A and 1B.

FIG. 1A shows an orthodontic analysis system using a device for predicting anatomical landmarks according to an embodiment of the present disclosure. FIG. 1B exemplarily shows the configuration of a device for predicting anatomical landmarks according to an embodiment of the present disclosure.

First, referring to FIG. 1A, a medical lateral head image of a subject can be obtained by a lateral head measurement radiograph apparatus 300. The obtained medical lateral head image can be a lateral cephalometric radiograph. The medical lateral head image of a lateral profile of the subject is transmitted to a device 100 for predicting anatomical landmarks according to an embodiment of the present disclosure.

The device 100 for predicting anatomical landmarks predicts a lateral facial region on the basis of the received medical lateral head image and predicts landmarks in the predicted lateral facial region.

Figure 1B:
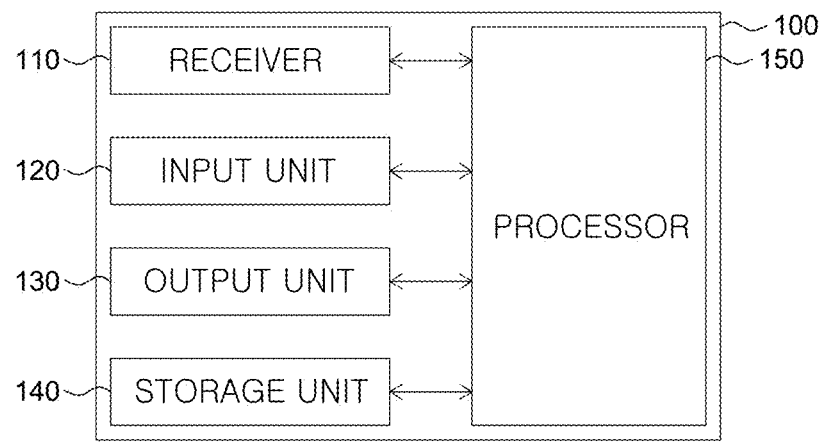
FIG. 1B exemplarily shows the configuration of a device for predicting anatomical landmarks according to an embodiment of the present disclosure.

In more detail, referring to FIG. 1B, the device 100 for predicting anatomical landmarks includes a receiver 110, an input unit 120, an output unit 130, a storage unit 140, and a processor 150.

In detail, the receiver 110 can be configured to receive a medical lateral head image of a subject from the lateral head measurement radiograph apparatus 300. As described above, the medical lateral head image obtained by the receiver 110 can be a lateral cephalometric radiograph, but is not limited thereto. Meanwhile, the receiver 110 can be further configured to transmit the obtained medical lateral head image to the processor 150 to be described below. Further, the receiver 110 may receive a medical lateral head image from the outside. The medical lateral head image obtained by the receiver 110 may include a lateral facial region.

The input unit 120 may set the device 100 for predicting anatomical landmarks and instruct the receiver 110 to perform the operations described above. Meanwhile, the input unit 120 can be a keyboard, a mouse, or a touch screen panel, but is not limited thereto.

On the other hand, the output unit 130 can visually show the medical lateral head image obtained from the receiver 110. Further, the output unit 130 can be configured to show the position information of a lateral facial region or landmarks determined in a medical lateral head image by the processor 150. However, the output unit 130 is not limited thereto and can be configured to show various items of information determined by the processor 150 for prediction of anatomical landmarks.

The storage unit 140 can be configured to store a medical lateral head image of a subject obtained by the receiver 110 and instructions of the device 100 for predicting anatomical landmarks set by the input unit 120. Further, the storage unit 140 is configured to store results predicted by the processor 150 to be described below. However, the storage unit 140 is not limited thereto and can store various items of information determined by the processor 150 for prediction of anatomical landmarks.

On the other hand, the processor 150 can be a component for providing an accurate prediction result for the device 100 for predicting anatomical landmarks. In order to predict anatomical landmarks, the processor 150 can be configured to predict a lateral facial region in a medical lateral head image and predict anatomical landmarks in the predicted facial region. For example, the processor 150 can be configured to use a prediction model learned to predict a lateral facial region in a medical lateral head image of a subject obtained from the receiver 110 and a prediction model learned to predict anatomical landmarks in a lateral facial region. The model learned to predict a lateral facial region can be based on a support vector machine algorithm and the model learned to predict landmarks can be based on a gradient boosting algorithm, but they are not limited thereto. For example, prediction models that are used in various embodiments of the present disclosure may be DNN (Deep Neural Network), CNN (Convolutional Neural Network), DCNN (Deep Convolution Neural Network), RNN (Recurrent Neural Network), RBM (Restricted Boltzmann Machine), DBN (Deep Belief Network), SSD (Single Shot Detector), and YOLO (You Only Look Once) models or a model learned to predict a lateral facial region and landmarks in a medical image, based on U-net.

On the other hand, according to various embodiments of the present disclosure, the device for predicting anatomical landmarks may further include a measurer configured to measure at least one selected from the size of the maxillofacial frame, the growth direction of the maxillofacial frame, and the degree of protrusion of sets of teeth of a subject on the basis of landmarks predicted by the processor 150.

Further, according to various embodiments of the present disclosure, the device for predicting anatomical landmarks may further include a data pre-processor configured to convert a medical lateral head image into a monochrome image and then vectorize the monochrome image when a medical lateral head image received by the receiver 110 is an RGB color image.

Figure 2A:
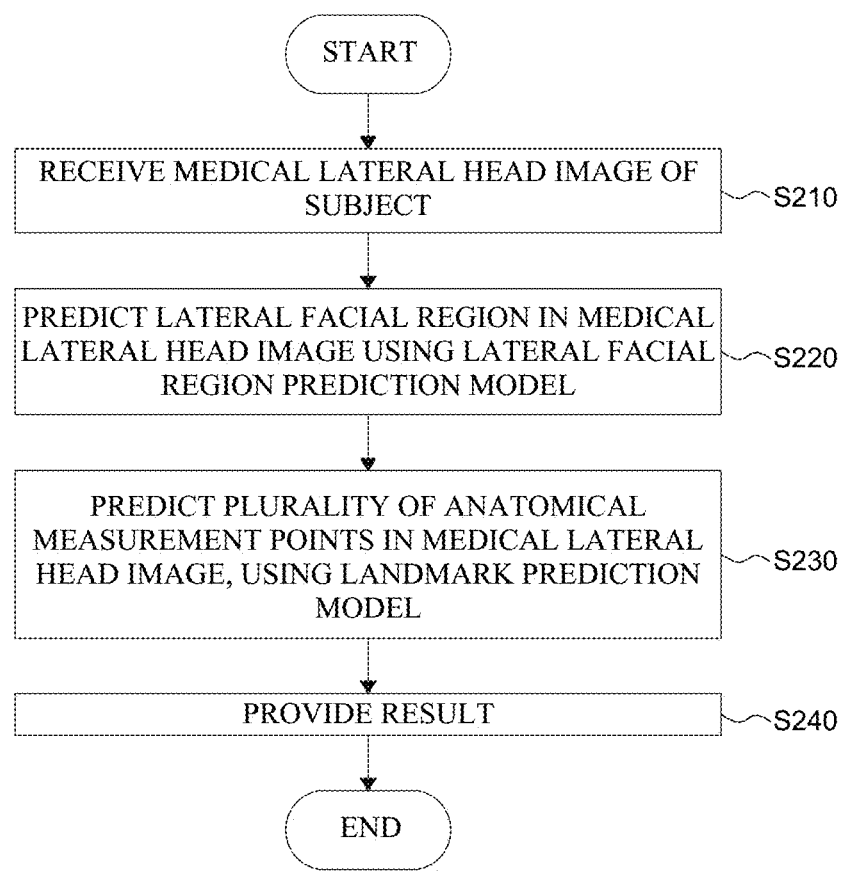
FIG. 2A shows a procedure of a method of predicting anatomical landmarks according to an embodiment of the present disclosure.
Figure 2B:
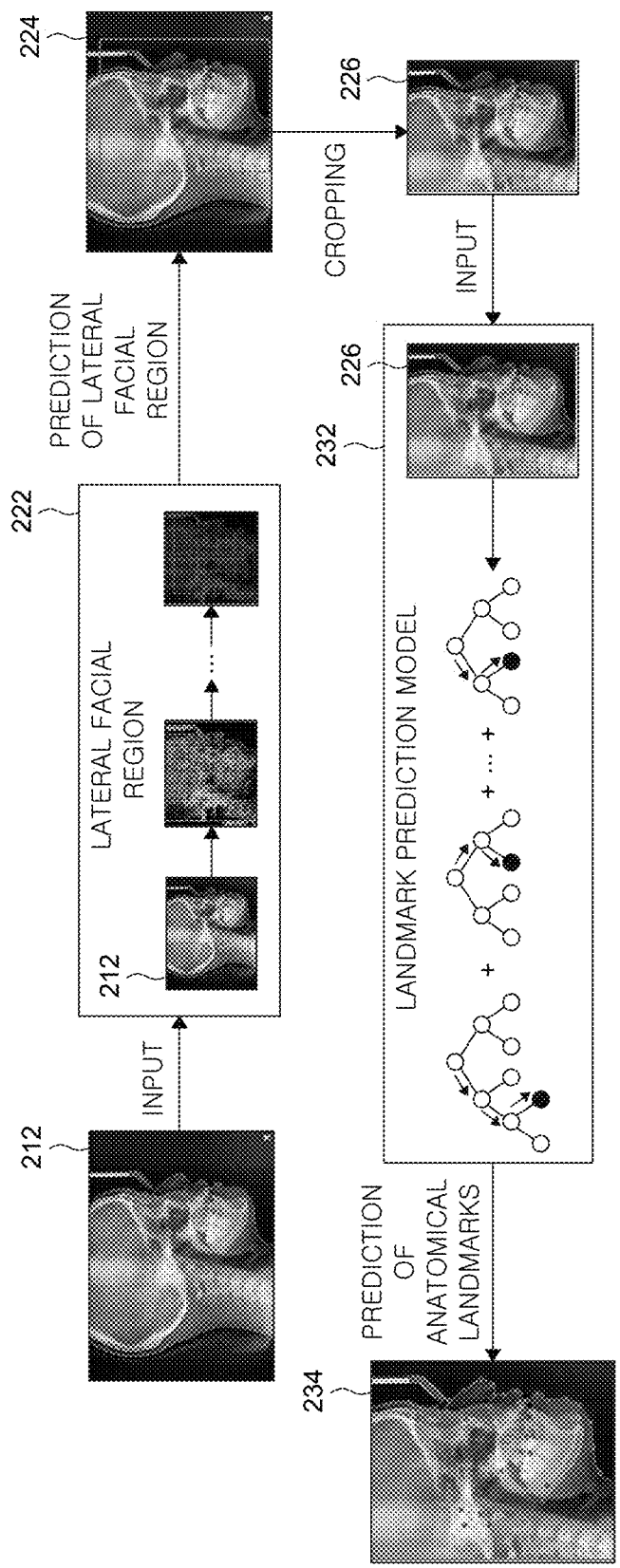
FIG. 2B exemplarily shows a procedure of predicting landmarks in a medical lateral head image by the method of predicting anatomical landmarks according to an embodiment of the present disclosure.

A method of predicting anatomical landmarks according to an embodiment of the present disclosure is described hereafter in detail with reference to FIGS. 2A and 2B. FIG. 2A shows a method of a method of predicting anatomical landmarks according to an embodiment of the present disclosure. FIG. 2B exemplarily shows a method of predicting anatomical landmarks in a medical lateral head image by the method of predicting anatomical landmarks according to an embodiment of the present disclosure.

Referring to FIG. 2A, a method of predicting anatomical landmarks according to an embodiment of the present disclosure is as follows. First, a medical lateral head image of a subject is received (S210). Next, a lateral facial region using a lateral facial region prediction model configured to predict a lateral facial region in the medical lateral head image is predicted (S220). Next, landmarks that are anatomical measurement points using a landmark prediction model configured to predict landmarks is predicted (S230). Finally, a predicted result is provided (S240).

For example, referring to FIG. 2B, a medical lateral head image 212 of a subject can be received in the receiving of a medical lateral head image (S210). The medical lateral head image 212 can be a lateral cephalometric radiograph, but is not limited thereto.

According to an embodiment of the present disclosure, in the receiving of a medical lateral head image (S210), it is possible to further receive a medical lateral head image 212, which has been pre-processed to have predetermined pixels, to be able to quickly analyze the medical lateral head image 212. If not so, a pre-process for the medical lateral head image 212 that adjusts the size to provide predetermined pixel units or adjusts contrast, resolution, brightness, and left-right symmetry can be further performed on the received medical lateral head image 212 after the receiving of a medical lateral head image (S210). For example, when the medical lateral head image 212 is an RGB color image, the medical lateral head image 212 can be converted into a monochrome image and vectorized in the pre-processing. In more detail, the medical lateral head image 212 converted in a monochrome image can be vectorized to a pixel having a largest brightness value of a plurality of pixels.

As a result of the pre-processing, the medical lateral head image 212 may have resolution or a size that is required by a prediction model to be described below and the resolution or the size can be smaller than those of the original medical lateral head image, so the processing speed of the prediction model can be improved.

Next, referring to FIG. 2B, in the predicting of a lateral facial region (S220), the medical lateral head image 212 obtained in the receiving of a medical lateral head image (S210) is input to a lateral facial region prediction model 222. The lateral facial region prediction model 222 can predict a lateral facial region on the basis of the coordinates of the lateral facial region in the medical lateral head image 212 and the pattern of the medical lateral head image 212, but is not limited thereto.

Meanwhile, a medical lateral head image 224 with a lateral facial region predicted is obtained as the result of the predicting of a lateral facial region (S220). The medical lateral head image 224 with a lateral facial region predicted can be cropped to include the lateral facial region.

Next, referring to FIG. 2B, a cropped lateral facial region 226 is input to a landmark prediction model 232 in predicting the landmarks (S230). The landmark prediction model 232 may predict the positions of the landmarks, in more detail, x-axial and y-axial coordinates on the basis of the cropped lateral facial region 226, but is not limited thereto.

According to an embodiment of the present invention, in predicting the landmarks (S230), an xml, json, or csv file including the landmarks, the x-axial and y-axial coordinates predicted by the landmark prediction model 232 can be created.

As the result of predicting the landmarks (S230), a medical lateral head image 234 with landmarks predicted can be obtained. The medical lateral head image 234 with landmarks predicted can be created by marking the positions of landmarks in the medical lateral head image 212 on the basis of the medical lateral head image 212 and the xml, json, or csv file created in predicting the landmarks (S230) described above, but is not limited thereto.

Referring to FIG. 2B again, in the providing of a predicted result (S240), the medical lateral head image 234 with landmarks predicted obtained in predicting the landmarks (S230) can be provided.

In the method of predicting anatomical landmarks according to an embodiment of the present disclosure, measuring at least one selected from the size of the maxillofacial frame, the growth direction of the maxillofacial frame, and the degree of protrusion of sets of teeth of a subject on the basis of measurement positions of predicted landmarks can be further performed.

By the method of predicting anatomical landmarks according to an embodiment of the present disclosure, it can be possible to predict with high accuracy anatomical landmarks in a medical lateral head image obtained from a subject and accurate measurement for orthodontics can be possible. Accordingly, the present disclosure can be applied to an orthodontic analysis system based on a medical lateral head image.

Figure 3A:
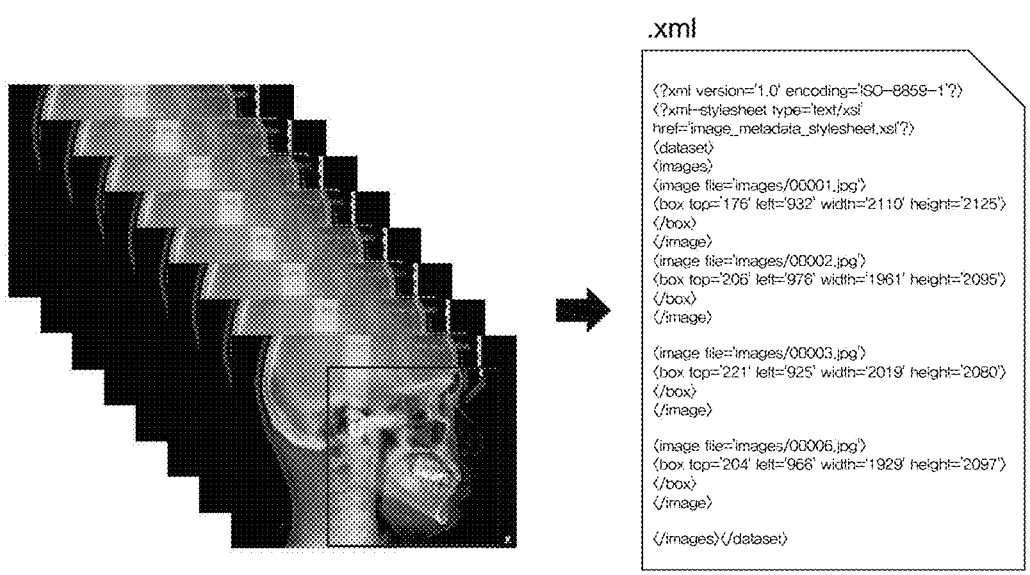
FIGS. 3A to 3C show a procedure of creating medical lateral head image data for learning a lateral facial region prediction model, the data being used in the method of predicting anatomical landmarks according to an embodiment of the present disclosure and the device for predicting anatomical landmarks using the method.
Figure 3B:
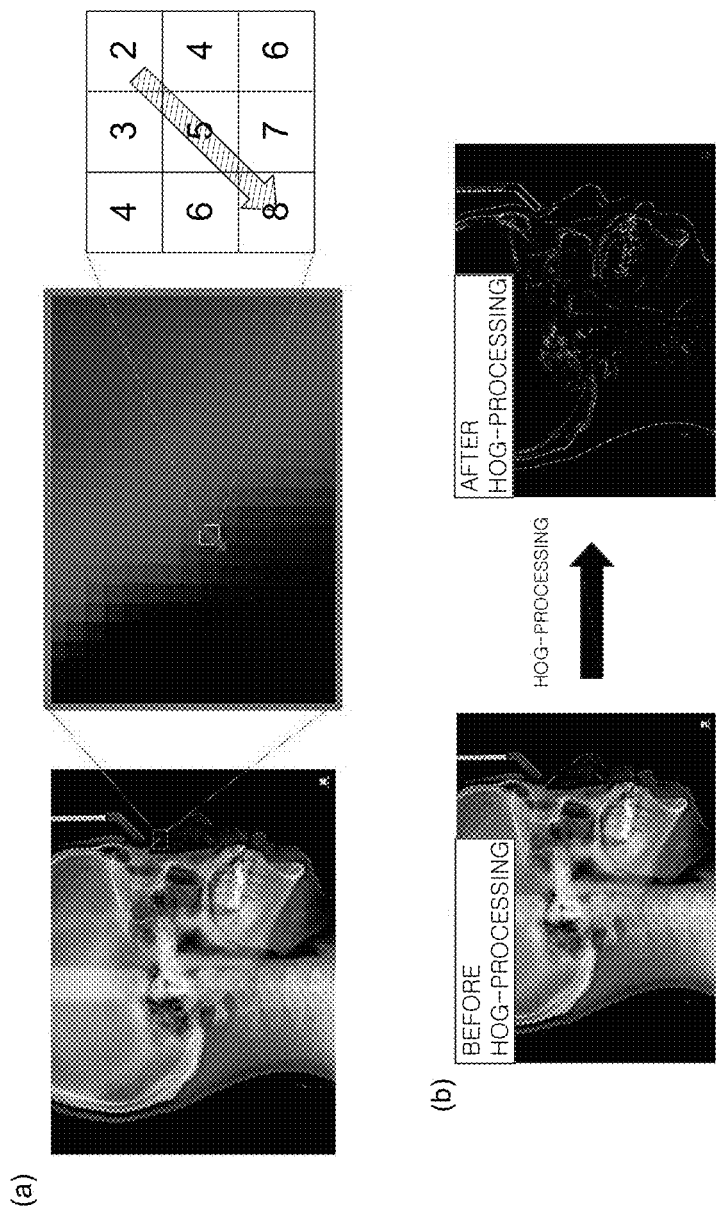
Figure 3C:
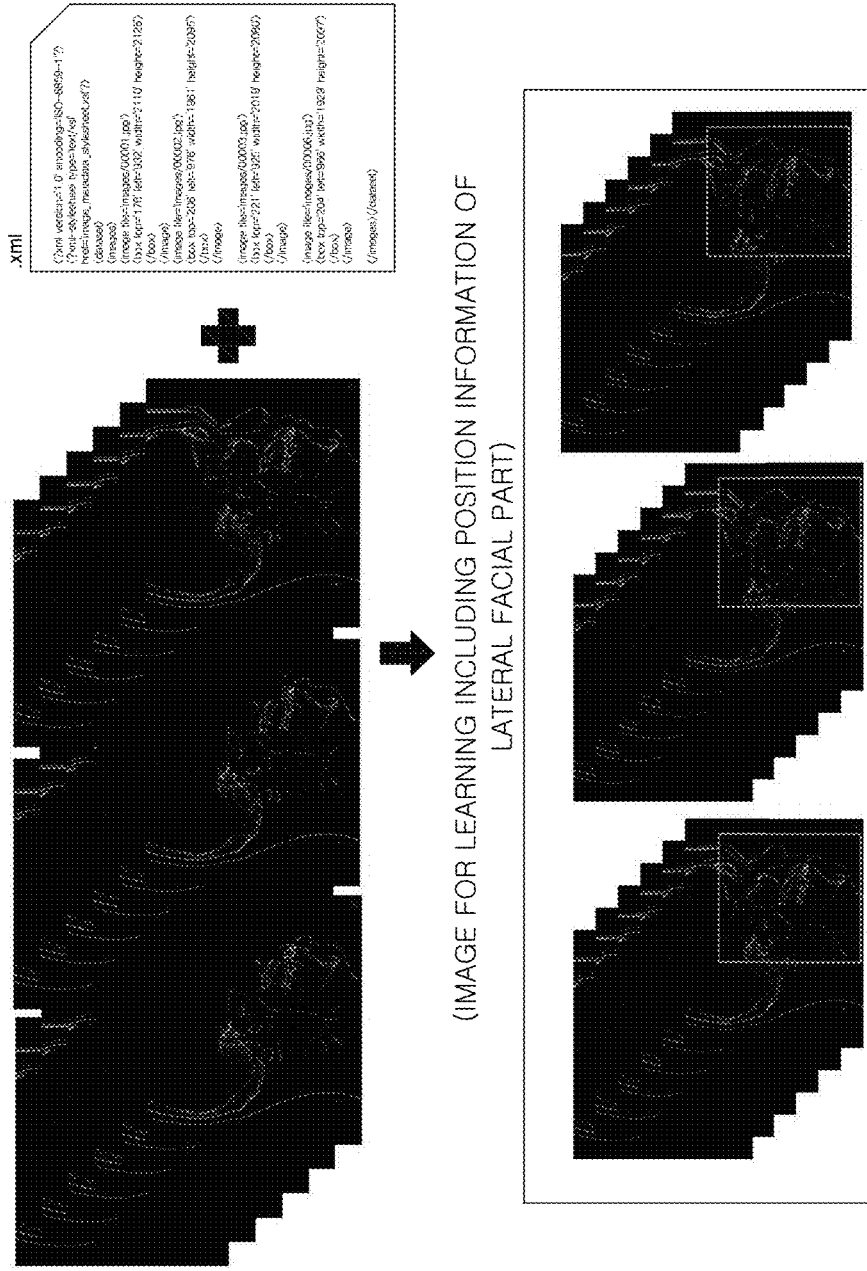

A learning method of a lateral facial region prediction model that is used in various embodiments of the present disclosure is described hereafter with reference to FIGS. 3A to 3C. FIGS. 3A to 3C show a procedure of creating medical lateral head image data for learning a lateral facial region prediction model, the data being used in the method of predicting anatomical landmarks according to an embodiment of the present disclosure and the device for predicting anatomical landmarks using the method.

Referring to FIG. 3A, first, a plurality of lateral cephalometric radiographs is prepared to learn a lateral facial region prediction model. Next, a lateral facial part including landmarks of measurement points is given coordinates in a rectangular region in the plurality of lateral cephalometric radiographs. Next, an xml file including the positions (image paths) where the plurality of lateral cephalometric radiographs are stored and coordinates of the lateral facial region (box) formed in each of the cephalograms is prepared. In more detail, the xml file may include the file names of the plurality of lateral cephalometric radiographs, and position values (top, left, width, and height) of the boxes formed for the lateral facial regions in the plurality of lateral cephalometric radiographs.

Meanwhile, referring to (a) and (b) of FIG. 3B, a pre-process such as HOG (Histogram of Oriented Gradient) conversion can be performed on the prepared plurality of lateral cephalometric radiographs. In the pre-process, brightness difference values of adjacent pixels of a plurality of pixels in the lateral cephalometric radiographs are calculated and converted, whereby the outline of the target of the lateral facial portion can be made clear. In more detail, in the pre-process, the lateral cephalometric radiographs can be converted into monochrome images, brightness value differences from adjacent eight pixels of a specific pixel among the pixels constituting the radiographs can be calculated, and the radiographs can be vectorized toward the largest brightness value difference (e.g., from number 2 to number 8 in (a) of FIG. 3B). As a result, it is possible to obtain a lateral cephalometric radiograph with a clear outline.

Referring to FIG. 3C, the positions of the lateral facial regions are marked on the basis of the xml file including the image paths and the coordinates of the lateral facial regions described above with reference to FIG. 3A, in the HOG-converted lateral cephalometric radiographs described with reference to FIG. 3B. As a result, medical lateral head images for learning for a lateral facial region prediction model which include position information of the lateral facial regions can be created.

Meanwhile, the lateral facial region prediction model can be based on an SVM algorithm configured to classify categories, that is, lateral facial regions by recognizing patterns of medical lateral head images for learning.

For example, prediction of a lateral facial region by the lateral facial region prediction model can be performed on the basis of an SVM machine learning algorithm of [Formula 1].

$$\underset{w,\xi,b}{\operatorname{argmin}}\left\{\frac{1}{2}\|w\|^2 + C\sum_{i=1}^{n}\xi_i\right\} \quad \text{[Formula 1]}$$

where, $y_i(w \cdot x_i - b) \geq 1 - \xi_i, \xi_i \geq 0$, for all $1 \leq i \leq n$.

This algorithm can be configured such that $$\frac{1}{2}\|w\|^2 + C\sum_{i=1}^{n}\xi_i$$

has a minimum value on [Formula 1].

A 'C-value' (C) that is a parameter that determines 'Cost' allowing for wrong classification of $$C\sum_{i=1}^{n}\xi_i$$

in machine learning can be 1. That is, the 'C-value' can be set as 1 in $$C\sum_{i=1}^{n}\xi_i$$

that means a cost function in [Formula 1]. Further, an 'epsion' (ξ) that is a parameter meaning a width without 'Cost' added can be 0.01 in the cost function of [Formula 1].

However, the learning factor values of the parameters that are input for learning are not limited.

A lateral facial region prediction model that is used in the method of predicting anatomical landmarks according to an embodiment of the present disclosure and a device for predicting anatomical landmarks using the method can predict a lateral facial region in a medical lateral head image with high accuracy by employing the algorithm described above. However, the lateral facial region prediction model is not limited thereto and can be learned in more various methods.

A learning method of a landmark prediction model that is used in various embodiments of the present disclosure is described hereafter with reference to FIGS. 4A to 4D. FIGS. 4A to 4D show a procedure of creating medical lateral head image data for learning a landmark prediction model, the data being used in the method of predicting anatomical landmarks according to an embodiment of the present disclosure and the device for predicting anatomical landmarks using the method.

Referring to FIG. 4A, landmarks set in advance to learn a landmark prediction model may include seventy five lateral cephalometric landmarks of an A-point, a B-point, an ANS (Anterior nasal spine), an AN (Antegonial notch), an articulare, a basion, a C (Cervical point), a condylion, a columella, a CL (Corpus Left), a dorsum of nose, a glabella, a gnathion, a gonion, an infradentale, an LICT (Lower incisor crown tip), an LIRT (Lower incisor root tip), an LMDP (Lower molar distal point), an LMMP (Lower molar mesial point), an Li (Labrale inferius), an Ls (Labrale superius), an LE (Lower embrasure), a lower lip, a menton, a nasion, a nasal bridge, an orbitale, a PM point, a PNS (Posterior nasal spine), a porion, a pogonion, a Pn (Pronasale), a Pt (Pterygoid point), an R1 point, an R3 point, an RD (Ramus down), a sella, an Sd (Supradentale), a soft tissue A point, a soft tissue B point, a Gn' (Soft tissue Gnathion), an Me' (Soft tissue Menton), an N' (Soft tissue Nasion), a Pg' (Soft tissue Pogonion), an Stmi (Stomion inferius), an Stms (Stomion superius), an SM point (Submandibular point), an Sn (Subnasale), a UICT (Upper incisor crown tip), a UIRT (Upper incisor root tip), a UMDP (Upper molar distal point), a UMMP (Upper molar mesial point), a UE (Upper embrasure), an upper lip, a mandibular outline 1, a mandibular outline 2, a mandibular outline 3, a mandibular outline 4, a mandibular outline 5, a mandibular outline 6, a maxilla outline 1, a maxilla outline 2, a maxilla outline 3, a maxilla outline 4, a maxilla outline 5, a maxilla outline 6, a maxilla outline 7, a maxilla outline 8, a maxilla outline 9, a maxilla outline 10, a maxilla outline 11, a symphysis outline 1, a symphysis outline 2, a symphysis outline 3, and a symphysis outline 4 that are anatomically determined in advance as measurement points for orthodontics. However, the anatomical landmarks are not limited thereto and can be easily changed in accordance with the anatomical structure of the face of a subject and the kind of an obtained medical lateral head image.

Figure 4B:
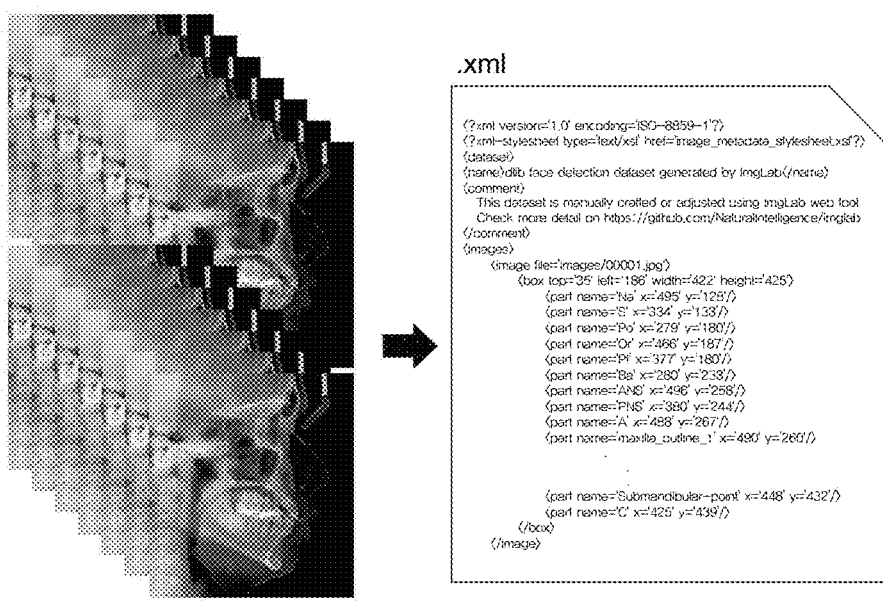

Referring to FIG. 4B, first, images with a lateral facial region cropped of a plurality of lateral cephalometric radiographs are prepared to learn a landmark prediction model. Next, coordinates of a plurality of landmarks are designated in the plurality of cropped lateral facial images. Next, an xml file including the positions (image paths) where the plurality of lateral facial images is stored and coordinates of the plurality of landmarks existing in each of the radiographs is prepared. In more detail, the created xml file may include the names of a plurality of lateral facial image files, the position values (top, left, width, and height) of boxes formed for the plurality of lateral facial images, that is, lateral facial regions, and the names and x-axial and y-axial coordinates of the plurality of landmarks.

Figure 4C:
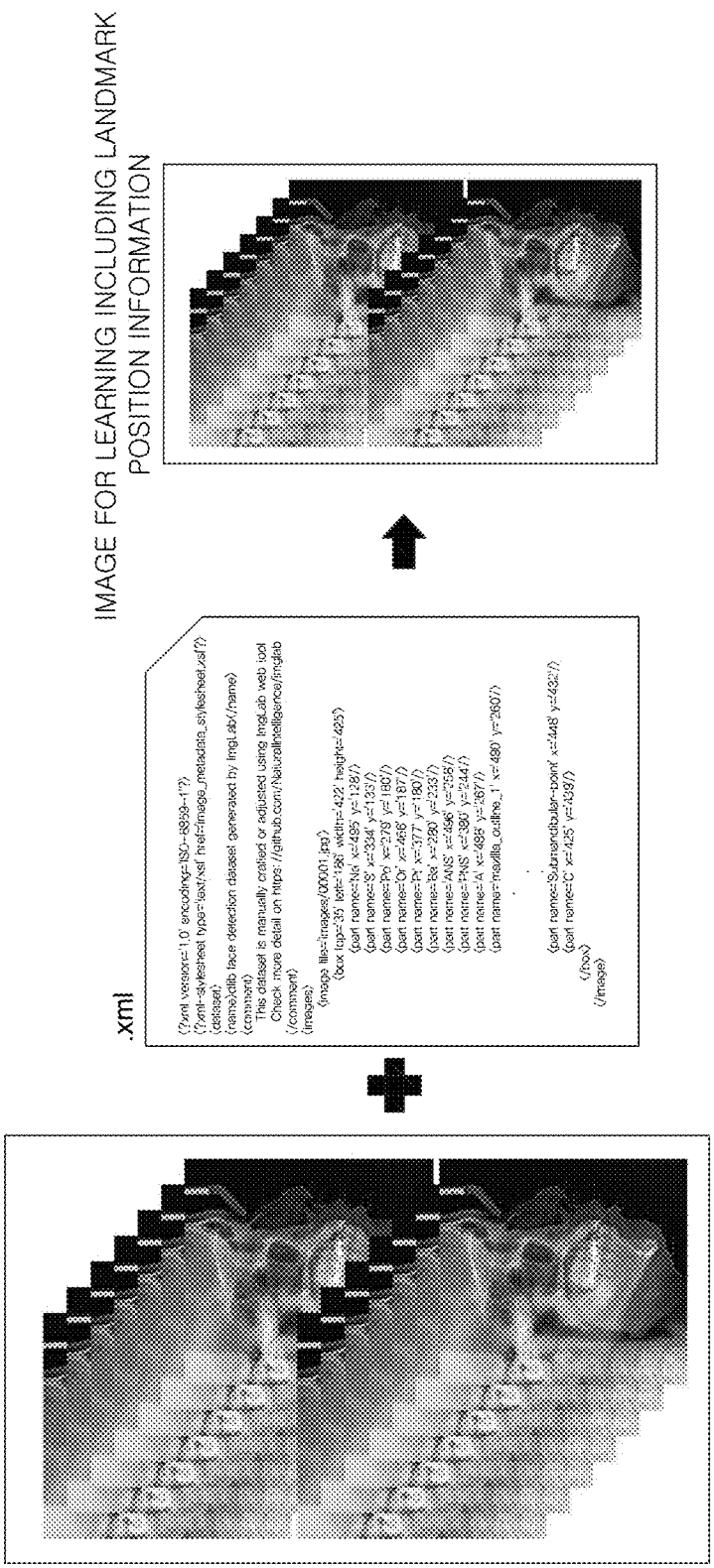

Referring to FIG. 4C, the positions of a plurality of landmarks are marked in the plurality of lateral facial images described with reference FIG. 4B on the basis of an xml file including image paths and x-axial and y-axial coordinates of a plurality of landmarks. As a result, medical lateral head images for learning for a landmark prediction model which includes position information of the plurality of landmarks can be created.

Meanwhile, the medical lateral head images for learning that are used to learn a landmark prediction model are not limited thereto.

Figure 4D:
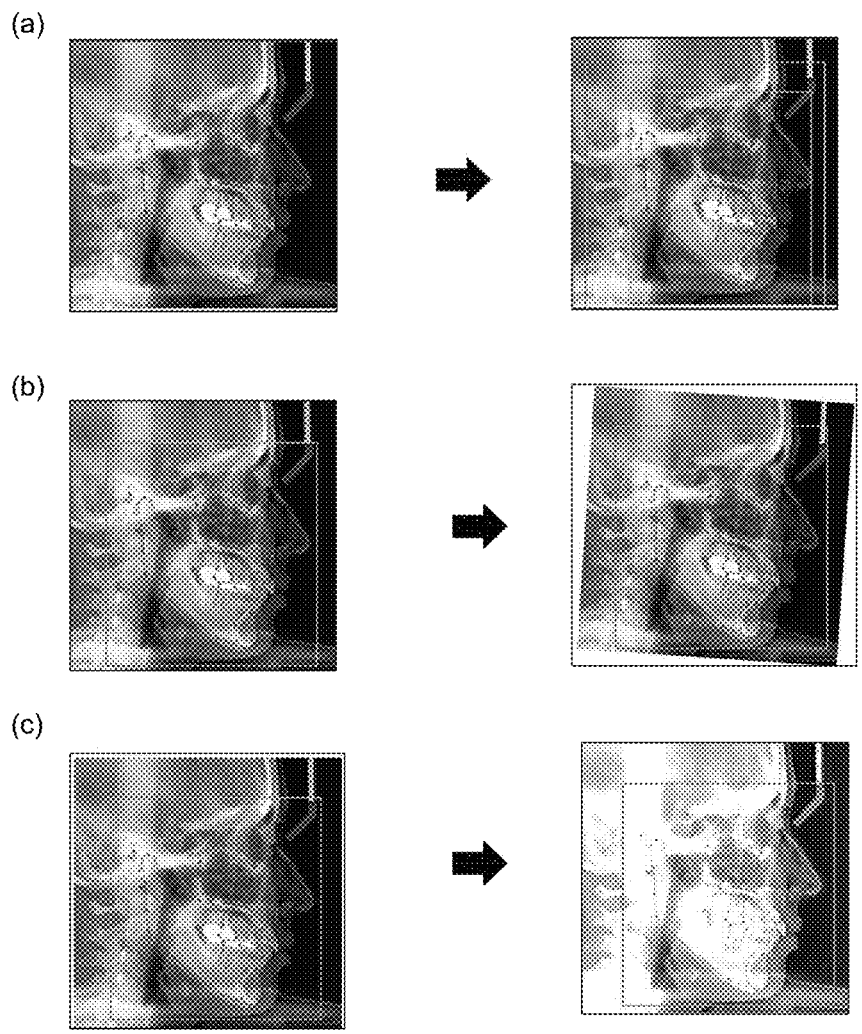

For example, referring to (a) of FIG. 4D, a medical lateral head image for learning can be an image of which the size of the image including a lateral facial region including landmarks is randomly determined. In more detail, a random box region (green box) between a region (yellow box) defined by a leftmost point, a rightmost point, an uppermost point, and a lowermost point and the outermost region (red box) of the original image can be set as a random function, whereby it can be used as an image for learning.

Referring to (b) of FIG. 4D, a medical lateral head image for learning a landmark prediction model can be rotated at a predetermined angle, for example, within 10 degrees from the same medical lateral head image. As a result, several medical lateral head images can be obtained by varying the angle. In more detail, the coordinates of an xml file are also rotated by varying an angle, several medical lateral head images including various items of position information of landmarks can be obtained. Accordingly, the prediction level can be improved with an increase in the amount of learning in the landmark prediction model.

Referring to (c) of FIG. 4D, the brightness and contrast of a medical lateral head image for learning a landmark prediction model may also be randomly determined from the same medical lateral head image. As a result, a plurality of medical lateral head images can be obtained by randomly determining the brightness and contrast. In more detail, a brightness value, contrast, a random gamma value of an image is adjusted (using a random function) with coordinates values of landmarks fixed in a medical lateral head image for learning. Accordingly, the landmark prediction model can be trained to predict landmarks from a random aspect ratio. As a result, the performance of the landmark prediction model is improved, the landmark prediction model may predict landmarks with high accuracy from various medical lateral head images.

Meanwhile, the landmark prediction model can be based on a gradient boosting algorithm configured to predict the positions of landmarks on the basis of a shape formed by a plurality of landmarks.

For example, the landmark prediction model may predict the positions of landmarks on the basis of the machining learning algorithm of gradient boosting of the following [Formula 2].

$$\hat{S}^{(t+1)} + \hat{S}^{(t)} + r_t(I, \hat{S}^{(t)})$$ [Formula 2]

where S is a shape formed by position values of a plurality of landmarks, I is a medical lateral head image for learning, and $\hat{S}^{(t)}$ is a shape predicted in a specific prediction step of a plurality of prediction steps. By adding a vector updated from a predicted shape formed before the specific prediction step through the algorithm, it is possible to obtain a next-step predicted shape and predict a shape finally formed by a plurality of landmarks.

'Cascade depth' that means the number of times of 'Cascade' that means a process of continuously performing prediction in machine learning can be 10. That is, t can be 10 in [Formula 2]. Further, an oversampling amount can be set as 500.

Meanwhile, the gradient boosting algorithm, which is an algorithm composed of k weak learners connected in a series, can be expressed as the following [Formula 3].

$$f_k(I, \hat{S}^{(t)}) = f_{k-1}(I, \hat{S}^{(t)}) + v \, g_k(I, \hat{S}^{(t)})$$ [Formula 3]

where $g_k$ (I, $\hat{S}^{(t)}$) may mean each weak learner. Further, 'v-value' (v) that means learning efficiency in the weak learners can be 0.1 and 'Number of trees per cascade level' (k) that means the number of the weak learners can be 500.

Meanwhile, the weak learners of $g_k$(I, $\hat{S}^{(t)}$) can be regression trees of a determination tree that determines priority of comparative characteristics in accordance with importance and goes down to a low characteristic by repeating a process of diversion according to a reference.

In prediction of landmarks, the comparative characteristic that is the reference of diversion at each node of the regression tree is a brightness difference between adjacent two pixels and 'Tree depth' that means the number of longest nodes from the uppermost node to the lowermost node in the regression tree can be set as 5.

However, the learning factor values of the parameters that are input for learning are not limited.

A landmark prediction model that is used in the method of predicting anatomical landmarks according to an embodiment of the present disclosure and a device for predicting anatomical landmarks using the method can predict landmarks in a medical lateral head image with high accuracy by employing the algorithm described above. However, the landmark prediction model is not limited thereto and can be learned in more various methods.

Embodiment 1: Prediction of position of landmark using lateral facial region prediction model and landmark prediction model.

Figure 5:
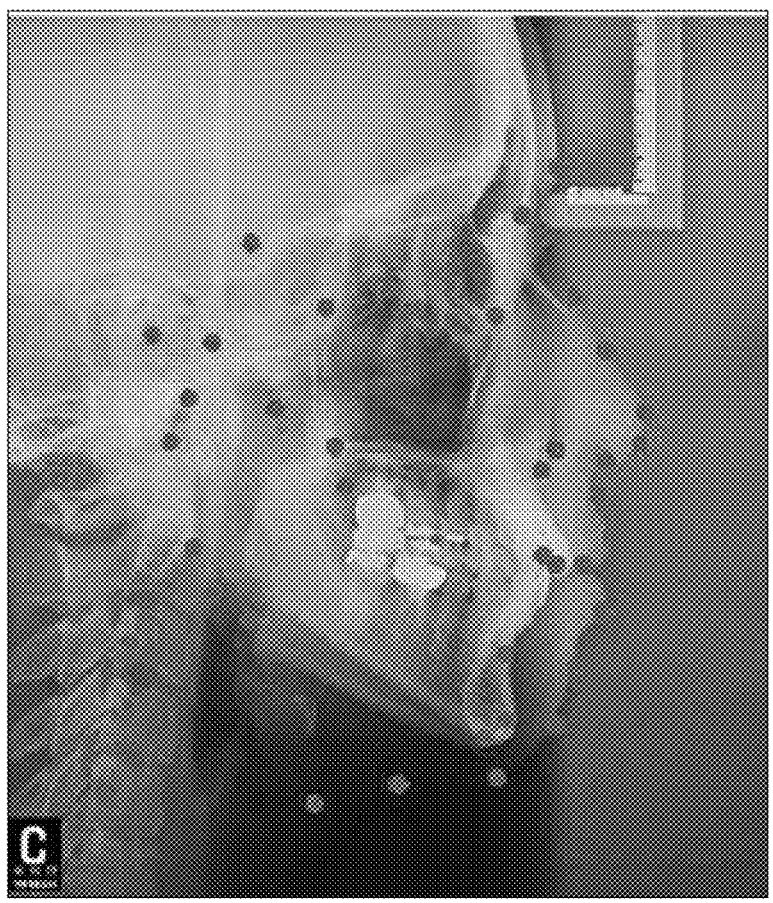
FIG. 5 shows landmarks predicted by the method of predicting anatomical landmarks according to an embodiment of the present disclosure and the device for predicting anatomical landmarks using the method.

Hereafter, a prediction result of the positions of landmarks using a lateral facial region prediction model and a landmark prediction model is described with reference to FIG. 5. FIG. 5 shows landmarks predicted by the method of predicting anatomical landmarks according to an embodiment of the present disclosure and the device for predicting anatomical landmarks using the method.

Referring to FIG. 5, a lateral facial region prediction model predicts a lateral facial region in a medical lateral head image of a subject and a landmark prediction model predicts a plurality of landmarks in the predicted lateral facial region. As a result, as a medical image with anatomical landmarks predicted is provided, medical personnel can obtain information for orthodontic analysis for the subject. However, the effect of the present disclosure is not limited thereto.

For example, according to the present disclosure, it can be possible to devise an accurate treatment plan for the subject before orthodontics by predicting and providing anatomical landmarks that are measurement points for orthodontic analysis. Accordingly, the present disclosure can contribute to providing an accurate and effective orthodontic method suitable for each subject's condition. For example, as anatomical landmarks are provided, medical personnel can more accurately and easily measure the size of a maxillofacial frame, measure the growth direction of the maxillofacial frame, and analyze the degree of protrusion of sets of teeth.

Further, the present disclosure has an effect that can predict and provide measurement positions of anatomical landmarks in a received medical lateral head image with high accuracy regardless of the proficiency of medical personnel.

Accordingly, the present disclosure can be applied to an orthodontic analysis system based on a medical lateral head image.

Although embodiments of the present disclosure were described in more detail with reference to the accompanying drawings, the present disclosure is not limited to the embodiments and can be modified in various ways without departing from the scope of the present disclosure. Accordingly, the embodiments described herein are provided merely not to limit, but to explain the spirit of the present disclosure, and the spirit of the present disclosure is not limited by the embodiments. Therefore, the embodiments described above are only examples and should not be construed as being limitative in all respects. The protective range of the present disclosure should be construed by the following claims and the scope and spirit of the present disclosure should be construed as being included in the patent right of the present disclosure.

What is claimed is:

1. A method of predicting anatomical landmarks, the method comprising:
receiving a medical lateral head image of a subject;
predicting coordinates of a lateral facial region in the medical lateral head image using a lateral facial region prediction model configured to predict the lateral facial region including a lateral facial part in the medical lateral head image;
predicting landmarks in the lateral facial region using a landmark prediction model configured to predict the anatomical landmarks in the medical lateral head image; and
providing an image with the landmark marked,
wherein the lateral facial region prediction model is a model learned by:
receiving the medical lateral head image for learning with coordinates of the lateral facial region determined in advance, and
predicting the lateral facial region in the medical lateral head image for learning on the basis of the coordinates of the lateral facial region and a pattern of the medical lateral head image for learning,
and wherein the medical lateral head image for learning is an image obtained by:
Histogram of Oriented Gradient (HOG) converting a sample medical lateral head image of a sample subject, and
marking the lateral facial region in the HOG-converted sample medical lateral head image on the basis of the coordinates of the lateral facial region in the sample medical lateral head image and a path of the sample medical lateral head image.

2. The method of claim 1, wherein predicting of the landmarks includes:
predicting x-axial and y-axial coordinates of the landmarks in the lateral facial region, on the basis of the medical lateral head image and the coordinates of the lateral facial region, using the landmark prediction model; and creating at least one file of xml, json, and csv files including the landmarks and the x-axial and y-axial coordinates, and wherein the providing of an image with the landmark marked further includes providing an image with positions of the landmarks marked in the medical lateral head image on the basis of the medical lateral head image and at least one file of the xml, json, and csv files.

3. The method of claim 1, wherein the landmark prediction model is a model learned to predict the landmarks in the medical lateral head image on the basis of a gradient boosting algorithm, and the lateral facial region prediction model is a model learned to predict the lateral facial region in the medical lateral head image on the basis of a support vector machine algorithm.

4. The method of claim 1, further comprising measuring at least one selected from a size of a maxillofacial frame, a growth direction of the maxillofacial frame, and a degree of protrusion of sets of teeth of the subject on the basis of the landmarks.

5. The method of claim 1, further comprising:

converting the medical lateral head image into a monochrome image; and vectorizing the monochrome image when the received medical lateral head image is an RGB color image.

6. A method of predicting anatomical landmarks, the method comprising:

receiving a medical lateral head image of a subject;

converting the medical lateral head image into a monochrome image when the received medical lateral head image is an RGB color image;

vectorizing the monochrome image;

predicting landmarks in the vectorized monochrome image using a landmark prediction model configured to predict the anatomical landmarks in the medical lateral head image; and providing an image with the landmark marked, wherein the vectorizing of the monochrome image includes:

calculating brightness difference values between a predetermined pixel of the monochrome image and a plurality of pixels adjacent to the predetermined pixel; and vectorizing the monochrome image toward a pixel of the plurality of adjacent pixels having a largest brightness difference value from the predetermined pixel.

7. The method of claim 1, wherein the landmark is at least one selected from the group consisting of an A-point, a B-point, an ANS (Anterior nasal spine), an AN (Antegonial notch), an articulare, a basion, a C (Cervical point), a condylion, a columella, a CL (Corpus Left), a dorsum of nose, a *glabella*, a gnathion, a gonion, an infradentale, an LICT (Lower incisor crown tip), an LIRT (Lower incisor root tip), an LMDP (Lower molar distal point), an LMMP (Lower molar mesial point), an Li (Labrale inferius), an Ls (Labrale superius), an LE (Lower embrasure), a lower lip, a menton, a nasion, a nasal bridge, an orbitale, a PM point, a PNS (Posterior nasal spine), a porion, a pogonion, a Pn (Pronasale), a Pt (Pterygoid point), an R1 point, an R3 point, an RD (Ramus down), a sella, an Sd (Supradentale), a soft tissue A point, a soft tissue B point, a Gn' (Soft tissue Gnathion), an Me' (Soft tissue Menton), an N' (Soft tissue Nasion), a Pg' (Soft tissue Pogonion), an Stmi (Stomion inferius), an Stms (Stomion superius), an SM point (Submandibular point), an Sn (Subnasale), a UICT (Upper incisor crown tip), a UIRT (Upper incisor root tip), a UMDP (Upper molar distal point), a UMMP (Upper molar mesial point), a UE (Upper embrasure), an upper lip, a mandibular outline 1, a mandibular outline 2, a mandibular outline 3, a mandibular outline 4, a mandibular outline 5, a mandibular outline 6, a maxilla outline 1, a maxilla outline 2, a maxilla outline 3, a maxilla outline 4, a maxilla outline 5, a maxilla outline 6, a maxilla outline 7, a maxilla outline 8, a maxilla outline 9, a maxilla outline 10, a maxilla outline 11, a symphysis outline 1, a symphysis outline 2, a symphysis outline 3, and a symphysis outline 4 that are determined in advance as lateral cephalometric landmarks for orthodontics.

8. The method of claim 1, wherein the landmark prediction model is a model learned by:

receiving the medical lateral head image for learning with coordinates of a plurality of landmarks predetermined in advance for a lateral facial region; and predicting coordinates of the plurality of landmarks in the medical lateral head image for learning on the basis of a shape formed by the coordinates of the plurality of landmarks in the medical lateral head image for learning.

9. A device for predicting anatomical landmarks, the device comprising:

a receiver configured to receive a medical lateral head image of a subject;

a processor connected to the receiver to communicate with the receiver; and a data pre-processor connected to the receiver and configured to:

convert the medical lateral head image into a monochrome image; and vectorize the monochrome image when the received medical lateral head image is an RGB color image, wherein to vectorize the monochrome image comprises to:

calculate brightness difference values between a predetermined pixel of the monochrome image and a plurality of pixels adjacent to the predetermined pixel; and vectorize the monochrome image toward a pixel of the plurality of adjacent pixels having a largest brightness difference value from the predetermined pixel;

wherein the processor is configured to predict landmarks in the medical lateral head image using a landmark prediction model configured to predict the landmarks in the medical lateral head image.

10. The device of claim 9, wherein the processor is further configured to predict coordinates of a lateral facial region in the medical lateral head image using a lateral facial region prediction model configured to predict the lateral facial region in the medical lateral head image, and to predict the landmarks in the lateral facial region using the landmark prediction model.

11. The device of claim 10, wherein the processor is further configured to: predict x-axial and y-axial coordinates of the landmarks in the lateral facial region, on the basis of the medical lateral head image and the coordinates of the lateral facial region, using the landmark prediction model; create at least one file of xml, json, and csv files including the landmarks and the x-axial and y-axial coordinates; and provide an image with positions of the landmarks marked in the medical lateral head image on the basis of the medical lateral head image and at least one file of the xml, json, and csv files.

12. The device of claim 9, further comprising a measurer configured to measure at least one selected from a size of a maxillofacial frame, a growth direction of the maxillofacial frame, and a degree of protrusion of sets of teeth of the subject on the basis of the landmarks.

13. The device of claim 9, wherein
- the landmark prediction model is a model learned to predict the landmarks in the medical lateral head image on the basis of a gradient boosting algorithm, and
- the lateral facial region prediction model is a model learned to predict the lateral facial region in the medical lateral head image on the basis of a support vector machine algorithm.

\* \* \* \* \*